(12) United States Patent
Sheehy et al.

(10) Patent No.: US 12,290,373 B2
(45) Date of Patent: May 6, 2025

(54) METHOD OF DETECTION, PROGNOSTICATION, AND MONITORING OF NEUROLOGICAL DISORDERS

(71) Applicants: C. Light Technologies, Inc., Berkeley, CA (US); The Regents of the University of California, San Francisco, CA (US)

(72) Inventors: Christy K. Sheehy, San Francisco, CA (US); Ari Green, Marin, CA (US); Zachary Helft, Berkeley, CA (US)

(73) Assignees: C. Light Technologies, Inc., Medford, MA (US); The Regents of the University of California, San Francisco, CA (US)

( * ) Notice: Subject to any disclaimer, the term of this patent is extended or adjusted under 35 U.S.C. 154(b) by 1097 days.

(21) Appl. No.: 17/050,828

(22) PCT Filed: Apr. 26, 2019

(86) PCT No.: PCT/US2019/029420
§ 371 (c)(1),
(2) Date: Oct. 26, 2020

(87) PCT Pub. No.: WO2019/210217
PCT Pub. Date: Oct. 31, 2019

(65) Prior Publication Data
US 2021/0228142 A1  Jul. 29, 2021

Related U.S. Application Data

(60) Provisional application No. 62/664,060, filed on Apr. 27, 2018.

(51) Int. Cl.
*A61B 5/00* (2006.01)
*A61B 5/11* (2006.01)
*A61B 5/16* (2006.01)

(52) U.S. Cl.
CPC .......... *A61B 5/4064* (2013.01); *A61B 5/1103* (2013.01); *A61B 5/163* (2017.08);
(Continued)

(58) Field of Classification Search
CPC ..... A61B 5/4064; A61B 5/1103; A61B 5/163; A61B 5/4082; A61B 5/4088; A61B 5/4094; A61B 5/4076
See application file for complete search history.

(56) References Cited

U.S. PATENT DOCUMENTS 7,857,452 B2  12/2010  Martinez-Conde et al.
8,226,236 B2  7/2012  Williams et al.
(Continued)

FOREIGN PATENT DOCUMENTS

AU  2015255024 B2  10/2020
CA  2827498 A1  8/2012
(Continued)

OTHER PUBLICATIONS

Ağaoğlu, M.N., Sheehy, C.K., Tiruveedhula, P., Roorda, A. and Chung, S.T. "Suboptimal eye movements for seeing fine details." Journal of vision, 18(5), pp. 8-8 (2018).
(Continued)

*Primary Examiner* — Jacqueline Cheng
*Assistant Examiner* — Tho Q Tran
(74) *Attorney, Agent, or Firm* — Resonance IP Law, PC

(57) ABSTRACT

Fixational eye movement may be analyzed to determine one or more characteristics thereof. Exemplary characteristics include measurements of microsaccade and drift measurement. These measurements may be correlated to a value for a diagnostic indicator for a neurological disorder or disease. These correlations may be used to diagnose, monitor, and prognosticate neurological disorders without administration of traditionally used neurological function tests or analysis
(Continued)

of biological samples by which the diagnostic indicators are typically determined.

5 Claims, 12 Drawing Sheets

(52) U.S. Cl.
CPC .......... *A61B 5/4082* (2013.01); *A61B 5/4088* (2013.01); *A61B 5/4094* (2013.01)

(56) References Cited

U.S. PATENT DOCUMENTS

| | | | |
|---|---|---|---|
| 8,696,122 | B2 | 4/2014 | Hammer et al. |
| 8,721,081 | B2 | 5/2014 | Martinez-Conde et al. |
| 8,818,492 | B2 | 8/2014 | Kim et al. |
| 9,301,679 | B2 | 4/2016 | Martinez-Conde et al. |
| 9,763,573 | B2 | 9/2017 | Distasi et al. |
| 9,962,119 | B2 | 5/2018 | Macknik et al. |
| 10,702,142 | B1* | 7/2020 | Kavusi ................. A61B 3/0041 |
| 2006/0082727 | A1 | 4/2006 | Bolger et al. |
| 2012/0238903 | A1 | 9/2012 | Martinez-Conde et al. |
| 2013/0218927 | A1 | 8/2013 | Patella et al. |
| 2014/0221869 | A1 | 8/2014 | Martinez-Conde et al. |
| 2014/0327881 | A1 | 11/2014 | Kiderman et al. |
| 2015/0029462 | A1 | 1/2015 | Distasi et al. |
| 2016/0106358 | A1 | 4/2016 | Macknik et al. |
| 2017/0000339 | A1 | 1/2017 | Statsi et al. |
| 2017/0135577 | A1* | 5/2017 | Komogortsev ........ A61B 5/168 |
| 2017/0188822 | A1 | 7/2017 | Yang |
| 2017/0273556 | A1* | 9/2017 | Macknik ............... A61B 5/4064 |

FOREIGN PATENT DOCUMENTS

| | | |
|---|---|---|
| CA | 2704777 C | 9/2017 |
| CA | 2855968 C | 6/2018 |
| EP | 2701578 A2 | 3/2014 |
| EP | 3110308 A4 | 4/2018 |
| EP | 2490584 B1 | 2/2019 |
| GB | 2527909 A | 1/2016 |
| JP | 2015512299 A | 4/2015 |
| JP | 2016523632 A | 8/2016 |
| WO | 2009059167 A1 | 5/2009 |
| WO | 2012103470 A2 | 8/2012 |
| WO | 2014193564 A1 | 12/2014 |
| WO | 2014204904 A1 | 12/2014 |
| WO | 2017100486 A1 | 6/2017 |
| WO | 2018112254 A1 | 6/2018 |

OTHER PUBLICATIONS

Braaf, B., Vienola, K., Sheehy, C.K., Yang, Q., Vermeer, K.A., Tiruveedhula, P., Arathorn, D.W., Roorda, A., & de Boer, J.F. "Real-time eye motion correction in phase-resolved OCT angiography with tracking SLO" Biomedical Optics Express, 4(1), 51-65 (2013).
Vienola, K., Braaf, B., Sheehy, C.K., Tiruveedhula, P., Arathorn, D.W., de Boer, J.F., & Roorda, A. "Real-time eye motion compensation in OCT imaging with tracking SLO". Biomedical Optics Express, 3(11)2950-2963 (2012).
PCT International Search Report and the Written Opinion of the International Searching Authority for International Application No. PCT/US2019/029420 dated Jul. 12, 2019.
Sheehy, C.K., Tiruveedhula, P., Sabesan, R., and Roorda, A. "Active eye-tracking for an adaptive optics scanning laser ophthalmoscope," Biomed. Opt. Express 6, 2412-2423 (2015).
Sheehy et al., "Methods to Assess Ocular Motor Dysfunction in Multiple Sclerosis," J. Neuro-Opthal., 38: 488-493, 2018.
Sheehy, C.K., Beaudry-Richard, A., Bensinger, E., Theis, J. and Green, A.J. "Methods to Assess Ocular Motor Dysfunction in Multiple Sclerosis." Journal of Neuro-Ophthalmology, 38(4), pp. 488-493 (2018).
Sheehy, C.K., Bensinger, E.S., Romeo, A., Rani, L., Stepien-Bernabe, N., Shi, B., Helft, Z., Putnam, N., Cordano, C., Gelfand, J.M., Bove, R., Stevenson, S.B., and Green, A.J. Fixational microsaccades: A quantitative and objective measure of disability in multiple sclerosis. Multiple Sclerosis Journal, 26(3), pp. 343-353 (2020).
Sheehy, C.K., Yang, Q., Arathorn, D.W., Tiruveedhula, P., de Boer, J.F., & Roorda, A. "High-speed, image-based eye tracking with a scanning laser ophthalmoscope." Biomedical Optics Express, 3(10) 2612-2622 (2012).
Stevenson, S.B., Sheehy, C.K., & Roorda, A. "Binocular eye tracking with the Tracking Scanning Laser Ophthalmoscope." Vision Res, 118: 98-104 (2016).

* cited by examiner

| Paraclinical Measures | # of subjects | Average # | | Average amplitude | | Average peak velocity | |
|---|---|---|---|---|---|---|---|
| | | p-value | r | p-value | r | p-value | r |
| Avg SDMT | 49 | 0.010 | 0.35 | 0.04 | 0.24 | 0.14 | 0.18 |
| Avg timed 25 foot walk | 77 | 0.12 | 0.18 | 0.44 | 0.12 | 0.61 | 0.08 |
| Avg 9-hole peg test dominant | 49 | 0.06 | 0.27 | 0.32 | 0.19 | 0.22 | 0.23 |
| Avg 9-hole peg test non-dominant | 49 | 0.006 | 0.39 | 0.60 | 0.10 | 0.32 | 0.18 |
| PASAT | 47 | 0.54 | 0.09 | 0.14 | 0.27 | 0.51 | 0.12 |
| GFI | 59 | 0.56 | 0.08 | 0.011 | 0.42 | 0.009 | 0.44 |
| History of ON | 101 | 0.38 | 0.24 | 0.15 | 0.16 | 0.17 | 0.17 |

Fig. 10

| FSS | # of subjects | Average # | | Average amplitude | | Average peak velocity | |
|---|---|---|---|---|---|---|---|
| | | p-value | r | p-value | r | p-value | r |
| Visual | 96 | 0.09 | 0.17 | 0.07 | 0.23 | 0.64 | 0.06 |
| Brainstem | 97 | 0.005 | 0.28 | 0.04 | 0.26 | 0.010 | 0.33 |
| Pyramidal | 98 | 0.009 | 0.26 | 0.62 | 0.06 | 0.93 | 0.01 |
| Cerebellar | 98 | 0.011 | 0.26 | 0.33 | 0.12 | 0.51 | 0.08 |
| Cerebral | 98 | 0.06 | 0.19 | 0.27 | 0.14 | 0.85 | 0.02 |
| Sensory | 95 | 0.53 | 0.06 | 0.61 | 0.06 | 0.35 | 0.12 |
| Bowel/bladder | 98 | 0.09 | 0.17 | 0.47 | 0.09 | 0.99 | 0.01 |

Fig. 12

METHOD OF DETECTION, PROGNOSTICATION, AND MONITORING OF NEUROLOGICAL DISORDERS

RELATED APPLICATION

This application is a non-provisional of, and claims priority to, U.S. Provisional Patent Application No. 62/664,060 entitled "METHOD OF DETECTION, prognostication, and monitoring of NEUROLOGICAL DISORDERS" filed Apr. 27, 2018, which is incorporated by reference, in its entirety, herein.

FIELD OF THE INVENTION

The present invention relates to a method for detecting, prognosticating, and monitoring a neurological disorder through the use of fixational eye motion measurements.

BACKGROUND

Today, physicians have a limited number of tools that are available to them to monitor and prognosticate the disease course of neurological disorders. The available tools include, for example, laborious physical function tests, lumbar punctures, blood tests, and MRI scans. These tools often produce imprecise results and are costly to administer.

BRIEF DESCRIPTION OF THE DRAWINGS

The present invention is illustrated by way of example, and not limitation, in the figures of the accompanying drawings in which:

FIG. 10 depicts a table including statistical parameters from Pearson's correlations, revealing whether associations exist between certain clinical measures (average SDMT, average time for 25-foot walk, average 9-hole peg test dominant, average 9-hole peg test nondominant, PASAT, GFI, history of optic neuritis (ON)) and certain TSLO recorded metrics (average amplitude of microsaccades, average velocity of microsaccades, and average number of microsaccades for a 10-second recording) after accounting for age, sex and disease duration, consistent with some embodiments of the present invention;

FIG. 12 depicts a table including Pearson's correlations, revealing whether associations exist between specific functional system scores (FSS) and certain TSLO recorded metrics (average amplitude of microsaccades, average velocity of microsaccades, and average number of microsaccades for a 10-second recording), when accounting for age, sex, and disease duration, consistent with some embodiments of the present invention;

Figure 1:
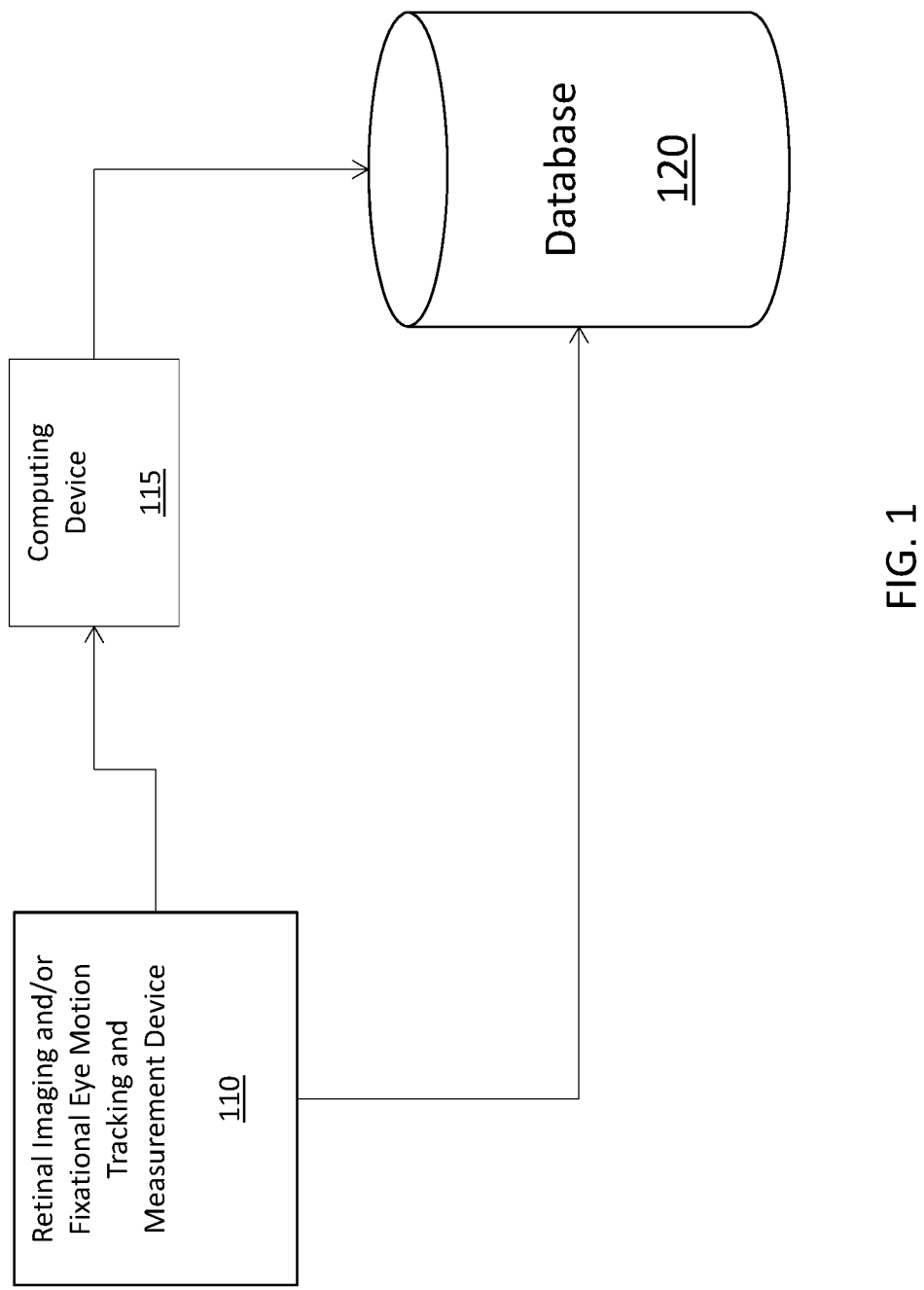
FIG. 1 depicts a block diagram of an exemplary system, consistent with some embodiments of the present invention.

Throughout the drawings, the same reference numerals and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

SUMMARY

Disclosed herein are systems, methods, and devices for detection, prognostication, and monitoring of neurological disorders. Exemplary neurological disorders include, but are not limited to, multiple sclerosis (MS), Parkinson's disease, Alzheimer's disease, dementia with Lewy bodies, frontotemporal dementia, Creutzfeldt-Jakob disease, vascular dementia, Wernicke-Korsakoff syndrome, amyotrophic lateral sclerosis (ALS), neuropsychiatric illnesses, Huntington's disease, brain damage, traumatic brain injury, mild traumatic brain injury, concussion, seizure disorders, cerebellar ataxia, epilepsy, peripheral neuropathy, movement disorders, demyelinating diseases, infections of the brain, stroke, and brain tumors and spinal cord tumors.

In some embodiments, a microsaccade and drift measurement may be received. The microsaccade and/or drift measurement may be first determined via analysis of retinal images of a use taken when the user's eyes are fixated on a point. Multiple retinal images, which are taken sequentially in time via, for example, a video recording, may be analyzed to determine how the eye moves when fixatated. This may be referred to herein as fixational eye motion. An estimate of a value for a diagnostic indicator of a neurological disease based on the microsaccade and drift measurement using a neurological disease model that correlates microsaccade measurements with estimated values for a diagnostic indicator of the neurological disease. One or more parameters of the neurological disease model may be trained using microsaccade and drift measurements of a subject that are paired with a value for a diagnostic indicator of the neurological disease of the subject.

In some embodiments, the microsaccade measurement may include a number of microsaccades in a time interval, an average number of microsaccades in a time interval, a peak number of microsaccades in a time interval, a raw or average amplitude of microsaccades in the time interval, a peak amplitude of microsaccades in the time interval, a velocity of microsaccades in the time interval, an average velocity of microsaccades in the time interval, a peak velocity of microsaccades in the time interval, a duration of microsaccades in the time interval, an average duration of microsaccades in the time interval, a peak duration of microsaccades in the time interval, an acceleration of microsaccades in the time interval, an average acceleration of microsaccades in the time interval, a peak acceleration of microsaccades in the time interval, a raw drift amplitude, an average drift amplitude, a peak drift amplitude, a drift duration, an acceleration in the vertical direction, a velocity in the vertical direction, a magnitude in the vertical direction, and/or a disconjugacy of any of the aforementioned motions between eyes.

At times, the value for the diagnostic indicator may correspond to a value of one or more of an expanded disability status scale (EDSS) score, a multiple sclerosis functional composite (MSFC) score, a raw symbol digit modality test (SDMT) score, an average SDMT score, a raw 9-hole peg test dominant score, an average 9-hole peg test dominant score, a raw 9-hole peg test nondominant score, an average 9-hole peg test nondominant score, a fatigue survey score, a global fatigue index (GFI) score, a functional systems score (FSS), a paced auditory serial addition test (PASAT) score, a lesion count, a lesion location, a lesion load, a percentage of atrophy of the user's brain, a percentage of atrophy of the user's spinal cord, a time to complete a 25 ft walk score, a serum-derived inflammatory marker score, a blood-derived inflammatory marker, a step count, optical coherence tomography (OCT) retinal layer thickness and angiography information, visually evoked potential (VEP) times/latencies, a cognitive score, a mood test score, an immediate post-concussion assessment and cognitive testing (ImPACT) score, a sport concussion assessment tool (SCAT) score, and/or a vestibular ocular motor screening (VOMS) score.

In some instances, a plurality of microsaccade measurements may be received and it may be determined whether a pattern is present in the plurality of microsaccade measurements. Exemplary patterns include, but are not limited to, a square wave jerk pattern, a square waves jerk train pattern, nystagmus, an ocular flutter pattern, an ocular tremor pattern, and an internuclear ophthalmoplegia pattern. The value for the diagnostic indicator of a neurological disease may be based on the determined pattern and/or a characteristic thereof. In some instances, the determination of the value for the diagnostic indicator of the neurological disease may be based on the determined pattern and a neurological disease model that correlates patterns with values for the diagnostic indicators of the neurological disease. At times, the values for the diagnostic indicators disclosed herein may be estimated and/or deduced based on a plurality of factors.

DETAILED DESCRIPTION

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. Description associated with any one of the FIG.s may be applied to a different FIG. containing like or similar components/steps.

Prior approaches for monitoring and prognosticating progression of a neurological condition and/or disorder like multiple sclerosis (MS), Alzheimer's disease, dementia, concussion, Parkinson's disease, dementia with Lewy bodies, frontotemporal dementia, Creutzfeldt-Jakob disease, vascular dementia, Wernicke-Korsakoff syndrome, amyotrophic lateral sclerosis (ALS), neuropsychiatric illnesses, Huntington's disease, brain damage, traumatic brain injury, mild traumatic brain injury, concussion, seizure disorders, cerebellar ataxia, epilepsy, peripheral neuropathy, movement disorders, demyelinating diseases, infections of the brain, stroke, and brain or spinal cord tumors clinical require in-office and bedside exams, blood and serum sample analysis, and analysis of magnetic resonance imagining (MRI) scans have been used. Lumbar punctures enable measurement of biomarkers in the cerebral spinal fluid (CSF), but are highly invasive and may result in complications. Likewise, MRI scans of the structure of the brain can be used to give coarse feedback on neurological health and/or disease progression. However, these tests are costly to perform, don't show high correlation with patient disability, and MRI's associated use of contrast agents are too dangerous for routine administration. As a result, patients are typically required to check in with their physician once or twice per year to monitor a patient's health and make determinations as to disease state and progression. With this schedule and tools, determinations as to a patient's responsiveness to treatment is imprecise, with the timeline for course correcting an ineffective treatment being, often times, too long. For example, it may take 2 years, or longer, before doctors have enough feedback (using traditionally available diagnostic tools) to determine whether a treatment is being effective.

In some instances, analysis of a patient's fixational eye motion (including microsaccades and drift) may be a useful biomarker for monitoring and prognosticating the neurological disease, such as MS, progression of a patient. Particular characteristics, features, and/or patterns of fixational eye motion (referred to collectively as "characteristics") may be determined from eye motion measurements, recordings, and/or traces, which recorded may record fixational eye motion ranging from 0.25 arcminutes. Exemplary characteristics of fixational eye motion include, but are not limited to, a raw and/or average number of microsaccades in a time period, raw or average velocity of microsaccades in a time period, raw or average amplitude of microsaccades in a time period, raw or average acceleration of microsaccades, drift amplitude, time spent making drift, and directionality of drift. These fixational eye motion characteristics may be correlated with one or more diagnostic indicators, disease disability scores, and/or neurostatus exam outputs, which may be collectively referred to herein as "diagnostic indicators." The correlated nature of these characteristics with diagnostic indicators may be helpful with monitoring and prognosticating neurological disease course.

Obtaining fixational eye motion measurements for a patient involves taking detailed images of the retina of the patient's left and/or right eyes to determine one or more characteristics of the patient's fixational eye motion. These measurements may be take using, for example, a tracking, scanning laser ophthalmoscope (TSLO) or other instrument configured to capture the fixational eye motion in a non-invasive manner. Because the measurements may be taken in a non-invasive manner, they avoid the potential complications of the aforementioned lumbar punctures, blood and scrum sample analysis. In addition, because TSLO instruments are relatively inexpensive to use when compared with MRI or other similar scanning/imaging machines, patients may affordably take more scans in a given period (e.g., monthly or weekly) than would be available for MRI scans. This may enable patients and doctors to more closely monitor disease progression and to capture information that may be useful to, for example, determine treatment effectiveness, likelihood of adverse events or relapse, etc.

Among other benefits, some benefits of using fixational eye motion measurements (microsaccades and drift) as a biomarker for monitoring and prognosticating the disease course of a neurological disorder like MS include providing quicker feedback on therapeutic efficacy, providing quicker feedback on the most effective type of medication a patient should be on, providing objective outcome measurements for clinical trials, predicting disease course, and showing finer detailed disease progression. The methods described herein may help to predict relapses, visualize the silent progression of disease, and may perhaps be an initial data point for a clinical diagnosis or prognosis.

The level of accuracy of the retinal image measurements is an important aspect of the present invention because, for example, it provides indications of small differences in the microsaccades, which may be an important indicator of neurological health and/or disease progression. The TSLO used to obtain the exemplary measurements discussed herein can track motion to within 0.25 arcminutes. The TSLO also uses the retina to track eye motion instead of the pupil. This enables absolute motion measurements as opposed to relative measurement (as is typically required with pupillary measurements) and with much greater accuracy. In addition, measurements of pupillary motion typically require calibration of the measurement device. Such calibration is not necessary when using the TSLO. Further advantages of using a TSLO include the level of accuracy, the level of precision, time and cost savings, and non-invasiveness.

Turning now to the figures, FIG. 1 provides a block diagram of an exemplary system 100 for obtaining retinal images and/or fixational eye measurements of one or more patients/users, communicating the retinal images and/or fixational eye measurement data, and/or executing one or more of the processes described herein. System 100 includes a retinal imaging and/or fixational eye motion tracking and measurement device 110, a computing device 115, and a database 120. Retinal imaging and/or fixational eye motion tracking and measurement device 110 may be any device configured to image a user's retina, or otherwise capture, fixational eye motion of the user and may be, for example, a TSLO, pupil-based trackers, optical levers, scleral search coils, optical coherence tomography, dual Perkinje trackers, or another type of scanning laser opthalmoscope such as an adaptive optics (AO) SLO. Computing device 115 maybe any computer, or processor, configured to perform one or more methods or processes, or portions thereof disclosed herein. In some embodiments, computing device 115 may be configured to receive one or more images of a user's retina and determine one or more fixational eye movement measurements therefrom. Further details regarding computing device 115 are provided below with regard to the discussion of FIG. 14. Database 120 maybe any data structure, or database configured to store, for example, retinal images, fixational eye motion measurements, diagnostic indicators, patient identifiable information, patient demographic information, and/or one or more determinations described herein.

Figure 2:
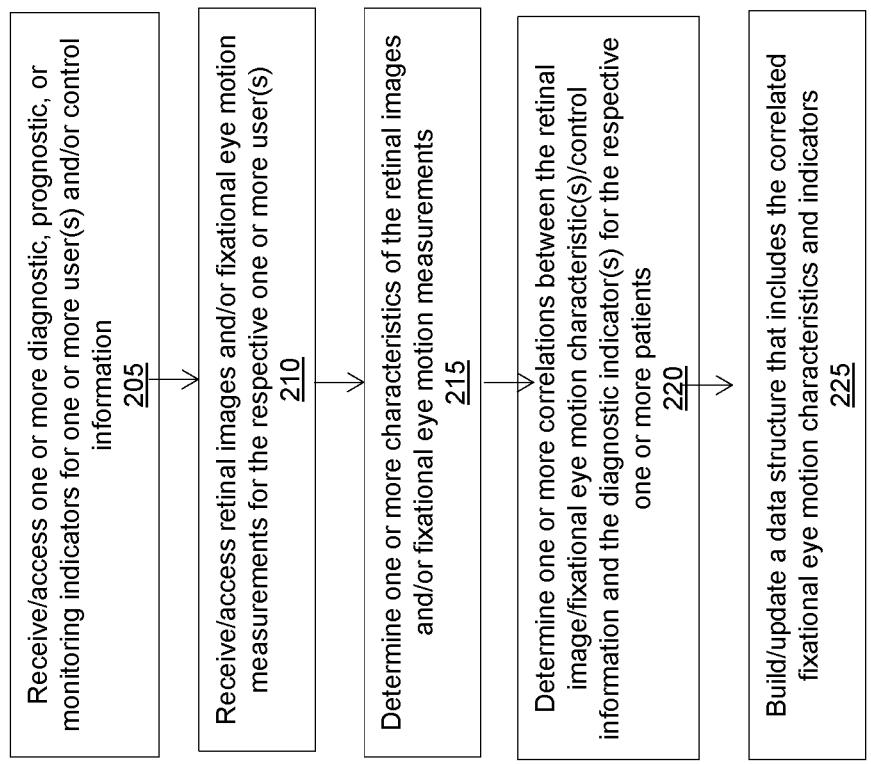
FIG. 2 depicts a flowchart showing a process for, consistent with some embodiments of the present invention.

FIG. 2 provides a flow chart illustrating a process 200 for determining one or more correlations between one or more fixational eye motion characteristic(s) and a diagnostic indicator. Process 200 may be executed by any of the systems or system components disclosed herein.

Initially, in step 205, one or more diagnostic indicators of neurological health and/or control information for subjects who are not suffering from a neurological disorder for one or more users may be received and/or access via, for example, querying a database like database 120. Diagnostic indicators include, but are not limited to, physiological (e.g., blood, urine, etc.) test results, performance (e.g., memory, coordination, mobility, etc.) test results, and health assessments performed by, for example, a physician, physical therapist, and/or user. Often times, the diagnostic indicators are indicators for diagnostic tools that are commonly, or traditionally used to diagnose and/or monitor neurological disease progression.

Figure 4:
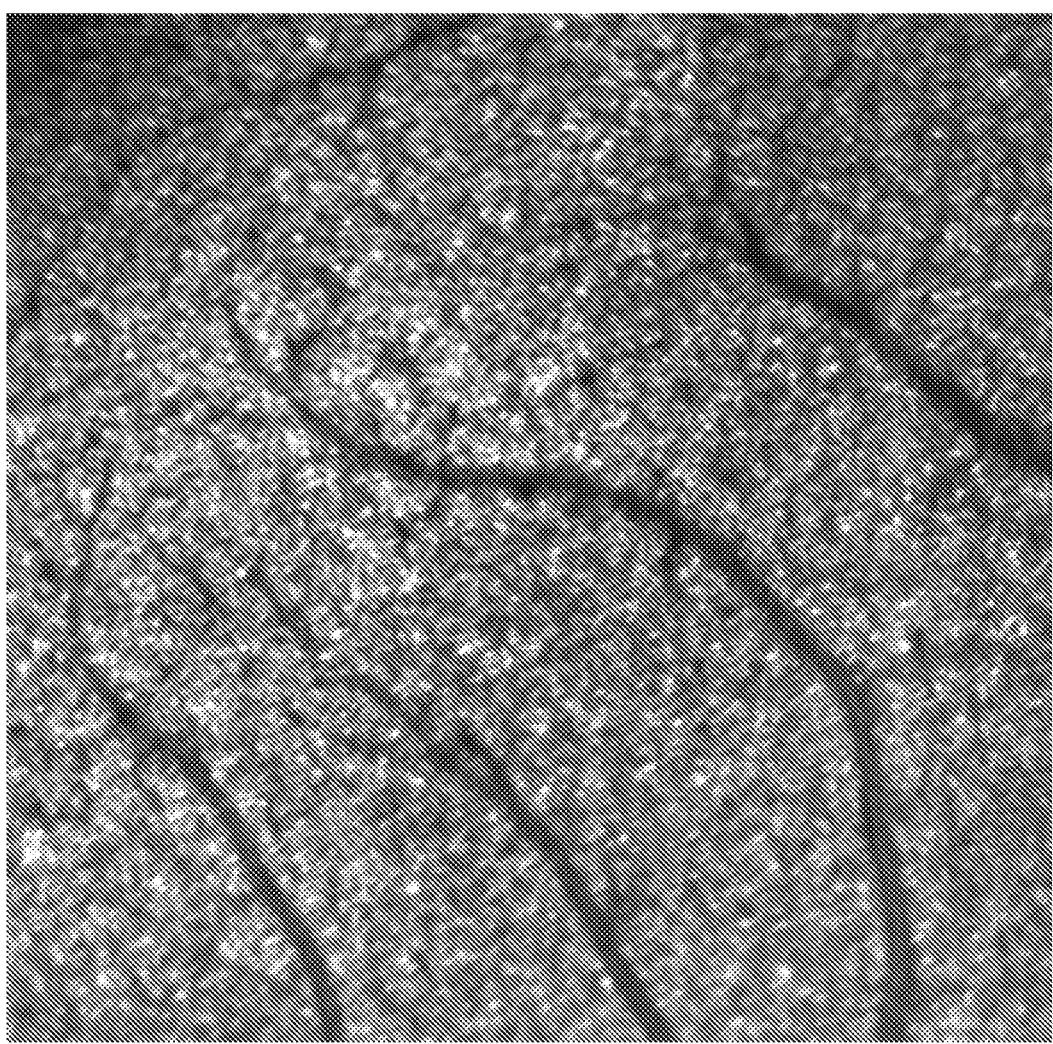
FIG. 4 depicts a registered stack of three hundred images of a control subject obtained using the TSLO system, consistent with some embodiments of the present invention.

In step 210, one or more retinal images and/or fixational eye motion measurements for one or more users may be received from, for example, retinal imaging and/or fixational eye motion tracking and measurement device 110 and/or via a query of a data structure like database 120. An example of a retinal image is provided by FIG. 4, which depicts an image 400 of a subject's retina that was obtained using a retinal imaging/fixational eye motion tracking and measurement device like retinal imaging/fixational eye motion tracking and measurement device 110. Retinal image 400 was captured by a retinal imaging/fixational eye motion tracking and measurement device 110 embodied as a TSLO system. More specifically, image 400 shows an average of a registered stack of 300 images of a control subject's retina obtained using the TSLO system. Retinal image 400 subtends 5×5 degree of the subject's retina.

In step 215, one or more characteristics of the retinal images and/or fixational eye measurements (sometimes referred to herein as microsaccade measurements) may be determined and/or measured. Fixation eye motion measurements may be determined by, for example comparing two or more retinal images of a subject taken at different points in time. Exemplary fixation eye motion/microsaccade measurements that may be received in step 210 and/or determined in step 215 include, but are not limited to, a number of microsaccades in a time interval, an average number of microsaccades in a time interval, a peak number of microsaccades in a time interval, a raw or average amplitude of microsaccades in the time interval, a peak amplitude of microsaccades in the time interval, a velocity of microsaccades in the time interval, an average velocity of microsaccades in the time interval, a peak velocity of microsaccades in the time interval, a duration of microsaccades in the time interval, an average duration of microsaccades in the time interval, a peak duration of microsaccades in the time interval, an acceleration of microsaccades in the time interval, an average acceleration of microsaccades in the time interval, peak acceleration of microsaccades in the time interval, a raw drift amplitude, an average drift amplitude, a peak drift amplitude, a drift duration, an acceleration in the vertical direction, a velocity in the vertical direction, a magnitude in the vertical direction, and a disconjugacy of any of the aforementioned motions between eyes.

Figure 5B:
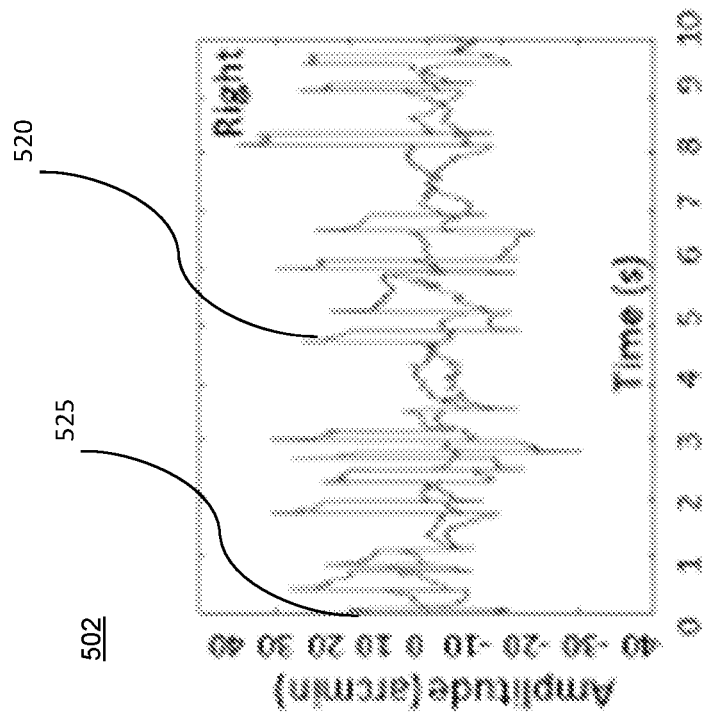
FIG. 5 depicts an experimental protocol for a subject, in which 10 seconds of retinal image data were recorded for the left eye, 10 seconds of retinal image data were recorded for the right eye, and the measurements were repeated three times per eye, consistent with some embodiments of the present invention.
Figure 5A:
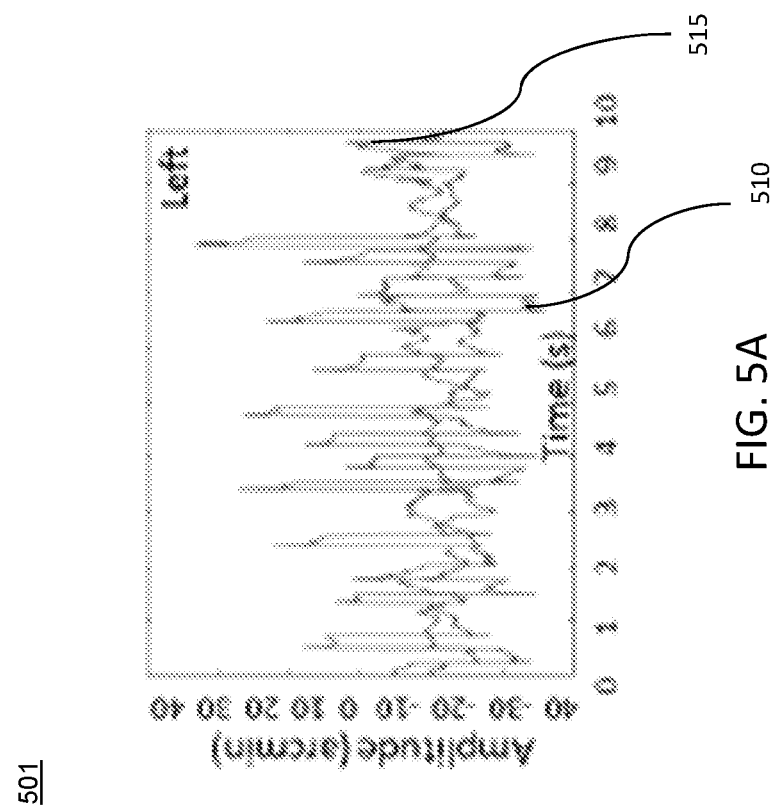

In some embodiments, the fixational eye motion measurements received in step 210 and/or determined in step 215 may be obtained by recording an image of a subject's left and/or right eye for a period of time (e.g., 5, 10, 20 seconds). In some embodiments, the recording may be repeated an appropriate number of times (e.g., 2, 3, 4, or 10 times) in order to, for example, obtain sufficiently clear or precise results. FIG. 5A provides a graph 501 showing an amplitude in arcminutes of microsaccade movements as a function of time within a 10 second interval for a subject's left eye and FIG. 5B provides a graph 502 showing an amplitude in arcminutes of microsaccade movements as a function of time within a 10 second interval for a subject's right eye. Graphs 501 and 502 provide raw data for how the left and right eye move over time wherein line 510 represents horizontal amplitude of the left eye's motion, line 515 represents the amplitude of vertical left eye motion, line 520 represents horizontal amplitude of the right eye's motion, line 525 represents the amplitude of vertical right eye motion. In some embodiments, these two traces/lines may be combined into a single vector, to generate a single amplitude over time measurement (not shown).

Figure 6:
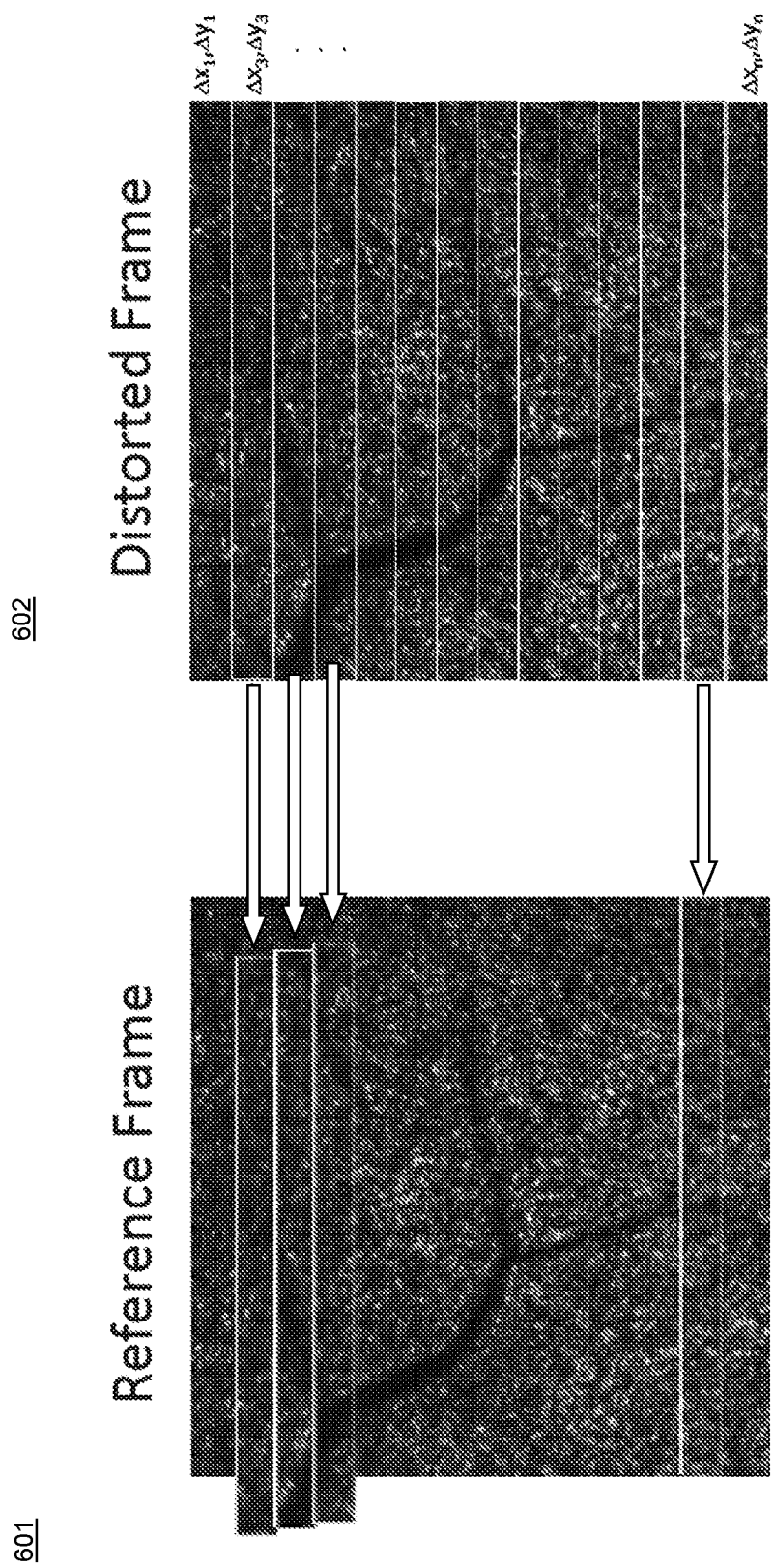
FIG. 6 depicts a process for extracting the fixational eye motion of a human subject from retinal image data by registering strip measurements of a subject's retina with corresponding strips present in a reference frame, consistent with some embodiments of the present invention.

FIG. 6 depicts a process for extracting the fixational eye motion of a subject from retinal image data, that may be received in step 210, by registering sequentially measured strips of the subject's moving retina (depicted in an image 602 under the heading "distorted frame") with corresponding strips present in an image 601 under the reference frame heading (in which the entire reference frame is taken within a short moment in time with minimal eye movement). The difference in the registered location on the reference frame of a measured strip and the registered location on the reference frame of an immediately subsequently measured strip reveals the motion of the subject's eye and the resultant fixational eye motion, which was extracted at a rate of 480 Hz (16 strips per frame) but can be performed at a higher rate of up to 1064 Hz depending on the number of strips chosen.

Following the extraction of fixational eye motion, microsaccades and drift may be detected, and then certain metrics regarding the detected microsaccades may be calculated, including the average number of microsaccades in a 10-second interval, the raw and average speed of eye motion during microsaccades in a 10-second interval, the raw and average acceleration of microsaccades, and the direction of microsaccades in microsaccades.

In step 220, a correlation between the retinal images/fixational eye motion characteristics of each of the users with his or her respective diagnostic indicator(s) and/or control information (which may not be patient specific) may be determined and, in step 225, a data structure (e.g., a database like database 120) may be built and/or updated that includes the correlated retinal images/fixational eye motion and diagnostic indicators along with, for example, an index and/or look-up table. An example of a correlation table showing correlations between fixational eye motion characteristics and diagnostic indicators is shown in FIG. 10 and discussed below with reference thereto.

In one embodiment, process 200 was executed by obtaining retinal images and/or fixational eye motion measurement for a group of control participants and a group of 111 participants diagnosed with MS (diagnosed by 2010 International Panel criteria) with 51 being assigned to Cohort 1 (C1), which had a mean (range) age of 46.6 (24-73), and 60 participants were assigned to Cohort 2 (C2) with mean (range) age of 52.4 (28-75). Overall, the mean (SD) age was 49.7 (12.7) years and 71.2% participants were women. Median (IQR) EDSS was 3 (2-5). A majority (68%) had relapsing-remitting MS (including CIS), 27% had progressive MS, and 3.6% had MS with yet undetermined course. Retinal imaging and eye-tracking was performed with the tracking scanning laser ophthalmoscope using 840 nm light to raster scan the retina. Three, 10-second long recordings of each subject's retina, spanning a 5-degree field of view, were acquired for each patient. Patients were instructed to fixate on the upper right-hand corner of the imaging raster. Strip-based, offline analysis of the retinal images was used to extract eye motion at 480 Hz. Microsaccadic metrics of velocity, speed, amplitude, quantity of microsaccades, directionality, acceleration, and overall fixation pattern were analyzed and compared to exemplary diagnostic indicators of Expanded Disability Status Scale (EDSS) scores and/or Functional System Scores (FSS) for each patient in both cohorts.

Both C1 and C2 demonstrated a clear correlation between the number of microsaccades recorded in a 10-second interval and a patient's EDSS score [Cohort 1 (C1) [r=0.46, p<0.001] and Cohort 2 (C2) [r=0.29, p=0.027], as well as with the two cohorts combined [r=0.35, p<0.001]). For paraclinical tests, the 9-hole peg test [non-dominant hand: r=0.39, p=0.006], Symbol Digit Modality Test [r=0.35, p=0.014], and EDSS Functional Systems Scores (FSS) including brainstem [r=0.28, p=0.005], cerebellar [r=0.26, p=0.011], and pyramidal [r=0.26, p=0.009], all showed associations with number of microsaccades. Additionally, brainstem FSS correlated with mean amplitude [r=0.26, p=0.04], mean velocity [r=0.33, p=0.010], and mean acceleration [r=0.31, p=0.016] of microsaccades. Compared to healthy controls, the average number of microsaccades [t (209)=−2.35, p=0.020], vertical acceleration [t (10562) =2.99, p=0.003], and vertical amplitude [t (10562)=−6.58, p<0.001] showed a statistically significant difference in patients with MS. In MS patients, amplitude [r=0.42, p=0.011], velocity [r=0.44, p=0.009], and horizontal acceleration [r=0.40, p=0.018] were also associated with fatigue, while controls no associations with fatigue.

Figure 7:
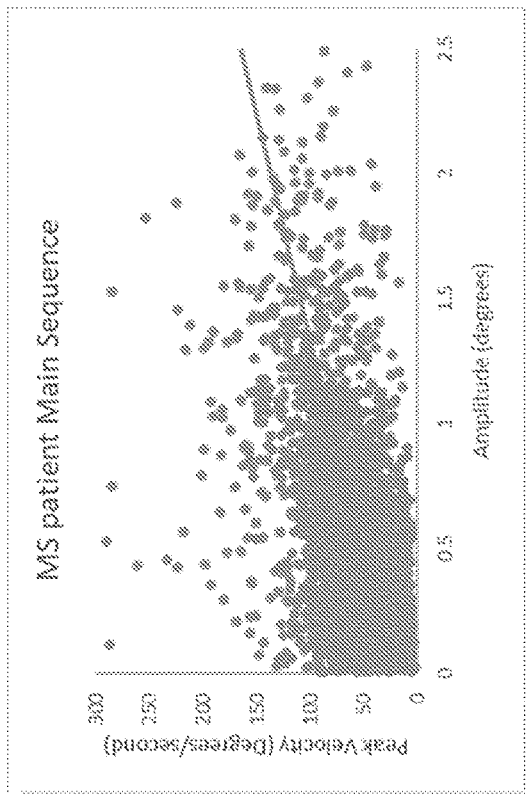
FIG. 7 depicts a scatter plot of the peak velocity versus amplitude of microsaccades for 4,779 microsaccades extracted from 100 control patients, consistent with some embodiments of the present invention.

FIG. 7 depicts a scatter plot of the peak microsaccade velocity versus the amplitude of microsaccades for 4,779 microsaccades extracted from 100 controls subjects, having an average age of 50.1 years. The scatter plot indicates that the peak velocity of microsaccades linearly increases with the amplitude of a microsaccades for control subjects.

Figure 8:
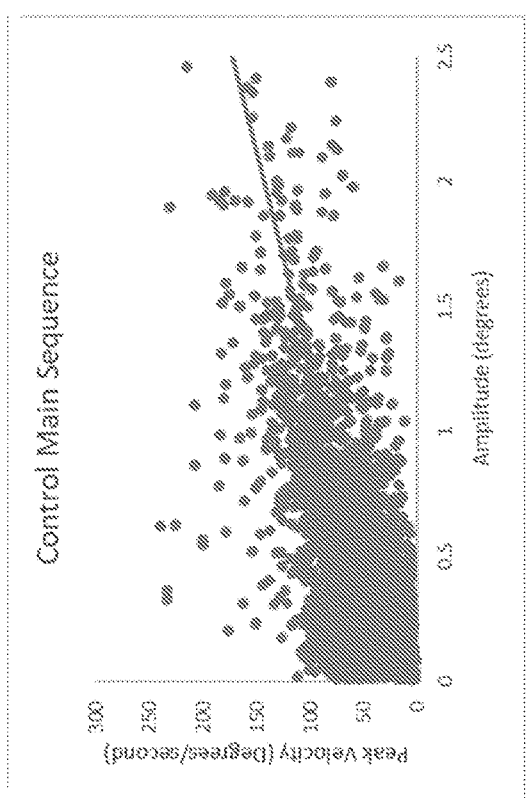
FIG. 8 depicts a scatter plot of peak velocity versus amplitude for 5,785 microsaccades extracted from 111 MS patients, consistent with some embodiments of the present invention.

FIG. 8 depicts a scatter plot of the peak microsaccade velocity versus the amplitude of microsaccades for 5,785 microsaccades extracted from the MS participants, which indicates that peak velocity of microsaccades linearly increases with the amplitude of a microsaccades for MS patients.

Figure 9:
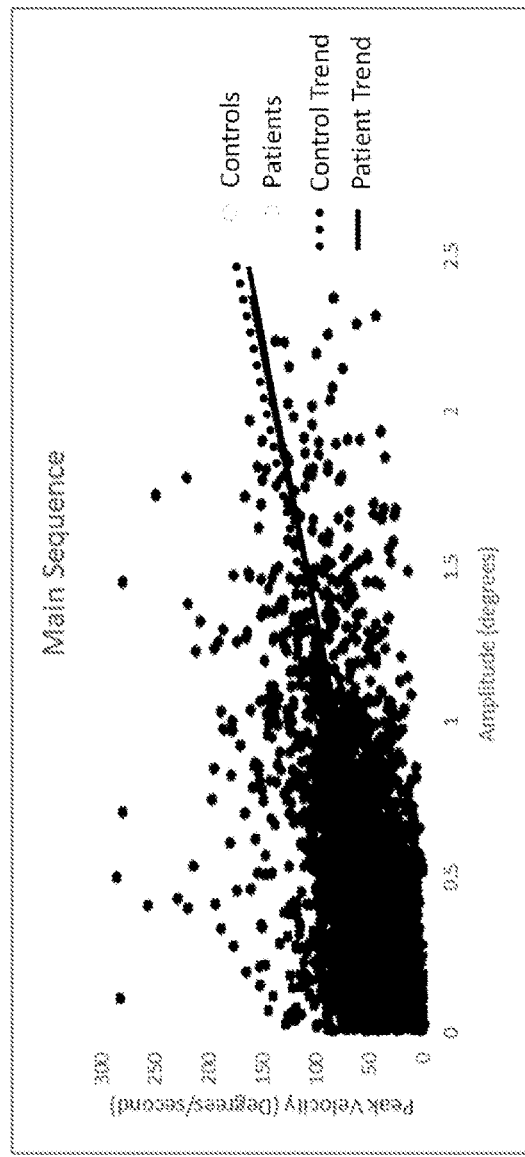
FIG. 9 depicts a scatter plot of peak velocity versus amplitude for microsaccades of both MS patients and control patients, along with a linear fit applied to each group, consistent with some embodiments of the present invention.

In FIG. 9, the scatter plot of FIG. 7 is overlaid with the scatter plot of FIG. 8 revealing a difference between the control subjects and the MS patients. Further, a linear regression line was plotted for the control subjects (with a $R^2$ value of 0.40-indicating a goodness of fit of the regression line to the data) and a linear regression line was plotted for the MS patients (with a $R^2$ value of 0.31). The linear regression lines indicate that for a given microsaccades amplitude, the main sequence relationship for MS patients was lower than the control group. One interpretation of the slope of the linear regression line is that the slope indicates a duration of microsaccades. The slope of the control's linear regression line being steeper than the slope of the MS patient's linear regression line may indicate that the duration of microsaccades, on average, was longer for control subjects than for MS patients. The data from FIGS. 7-9 shows how microsaccades measurement may be correlated to the presence of a neurological disease itself (not merely a biomarker to track the progression of a neurological disease).

When running an unpaired t-test with the data shown in the table of FIG. 10 (which represents peak velocity and amplitude values for 4,779 microsaccades for the control group) and the graph of FIG. 11 (which represents peak velocity and amplitude values for 5,785 microsaccades for both cohorts of patients), it was determined that statistically significant relationships (e.g., a p-value is 0.05 or below) between the control group and MS patient cohorts exist as follows:

the difference in the vertical component of the microsaccadic amplitude between MS patients vs. controls was statistically significant [8.0 arcmin (7.7-8.2) vs 6.7 arcmin (6.5-6.9), t (10562)=−6.58, p<0.001].

MS participants' vertical component of acceleration [$9,903.3°/s^2$ (9,696.8-10,109.9) vs $10,375.9°/s^2$ (10,143.8-10,608.0), t (10562)=2.99, p=0.003] also showed a statistically significant difference compared to controls. This shows that vertical microsaccadic acceleration in MS patients was dampened compared to the control population.

The average number of microsaccades in a 10 second recording was higher in participants with MS relative to participants without MS [mean (95% confidence interval (CI)) 14.3 (12.8-15.8) vs. 11.9 (10.7-13.1); t (209) =−2.35, p=0.020], with an average increase of 2.4 microsaccades for those with MS.

These calculations show statistical relationships for the amplitude, acceleration, and duration between MS patients and controls with and without averaging. Thus, the methods disclosed herein include analysis of the raw data quantities and average data quantities when making comparisons between controls and patients. One or more of these relationships may be used to diagnose, prognosticate, or monitor a person being evaluated for a neurological disorder, such as MS.

FIG. 10 depicts a table 1000 including statistical parameters from Pearson's correlations made using the data gathered from the cohorts, revealing whether correlations exist between exemplary diagnostic indicators (referred to on the table as paraclinical measures) and certain TSLO recorded metrics (average number of microsaccades, average amplitude of microsaccades, and average velocity of microsaccades). The exemplary diagnostic indicators included in the table of FIG. 10 are average symbol digit modality test (SDMT) score, the average time of a 25-foot walk test, the average 9-peg test dominant score, the average 9-peg test nondominant score; the paced auditory serial addition test (PASAT) test and the global fatigue index (GFI), and the presence of optic neuritis (ON). The Pearson's correlations remove the variability introduced by age, sex, and MS disease duration. Not pictured: the horizontal component of acceleration correlated with GFI [r=0.40, p=0.018] for the MS cohort (N=58).

Generally, the lower the p-values, the stronger the correlation between two variables. Therefore, table 100 reveals that the average number of microsaccades in a given time period is correlated with the SDMT score, the average 9-peg test non-dominant score; the average microsaccades amplitude in a given time interval is correlated with the SDMT and GFI; and the average microsaccades velocity and horizontal acceleration in a given time interval is correlated with the GFI. These correlations indicate that the average number of microsaccades in a given time interval may be used to estimate a value for a diagnostic indicator of MS, such as the average SDMT score and the average 9-hole peg test non-dominant score. The above-described correlations further indicate that the average microsaccades amplitude in a given time interval may be used to estimate a value for a diagnostic indicator of MS, such as the GFI score. The above-described correlations further indicate that the average microsaccades velocity and horizontal acceleration in a given time interval may be used to estimate a value for a diagnostic indicator of MS, such as the GFI score. The number of subjects for each of the rows indicates the number of subjects out of the 111 MS patients who completed the corresponding evaluation. For example, 49 out of the 111 MS patients completed the SDMT.

Figure 11:
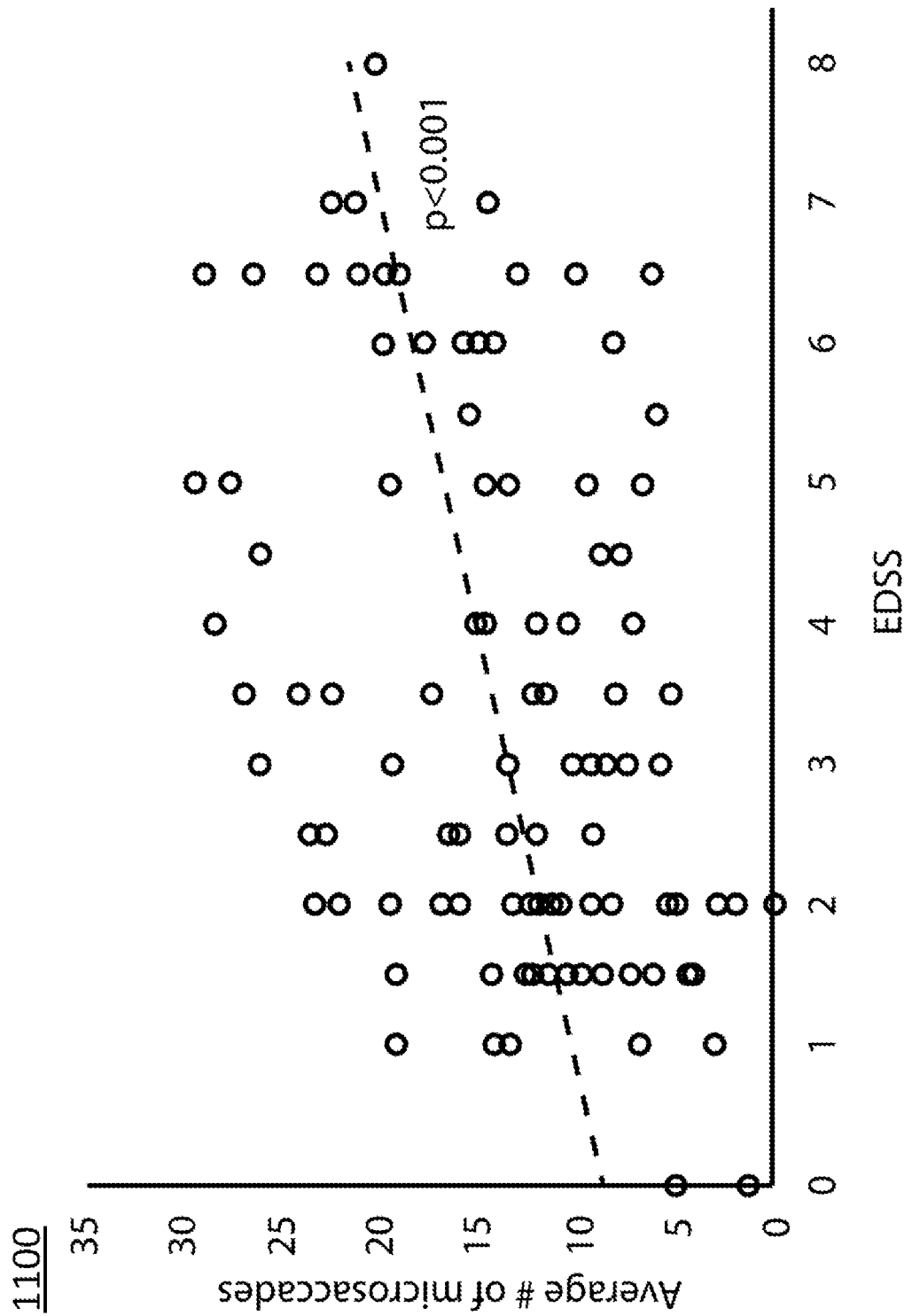
FIG. 11 depicts a scatter plot of the average number of microsaccades for 111 MS patients during a 10-second (300 frame) recording versus with patient disability as quantified by the EDSS score ($p<0.001$) when accounting for age, sex and disease duration, consistent with some embodiments of the present invention.

FIG. 11 depicts a scatter plot of the average number of microsaccades in a 10-second (300 frames) time period versus the expanded disability status scale (EDSS) score. By way of background, an EDSS score of 0-1 indicates no disability, 2 indicates minimal disability, 3 indicates moderate disability, 4 indicates a significant disability, 5 indicates a disability serious enough to impair full daily activities, 6 indicates a disability that requires a walking aid, 7 indicates a disability in a person is unable to walk beyond approximately 5 meters even with aid.

A linear regression line is depicted in FIG. 11 showing that the average number of microsaccades in a given time period generally increases with the severity of MS (i.e., higher EDSS score). The linear regression line can be interpreted as a model which correlates the average number of microsaccades in a given time period with a value for a diagnostic indicator of MS (e.g., the EDSS score). Given a measurement of the average number of microsaccades in a given time period, the model can be used to estimate the EDSS score. For example, for a subject with an average of 10 microsaccades, the EDSS score can be estimated to be 0; for a subject with an average of 17 microsaccades, the EDSS score can be estimated to be 6.

FIG. 12 depicts a table 1200 that includes the statistical parameters from Pearson's correlations of the functional system scores (FSS) that comprise the EDSS score. 95-98 subjects participated in the FSS assessment. Pearson's correlations adjusting for age, sex, and MS disease duration were performed. Statistically significant results at or below the p<0.05 threshold is in bold and underlined for clarity. The average number of microsaccades was positively associated with the FSS of interest, brainstem [r=0.28, p=0.005] and cerebellar [r=0.26, p=0.011] function, as well as with the pyramidal FSS [r=0.26, p=0.009]. Brainstem was also statistically correlated with mean amplitude (dominated by horizontal motion) [x component: r=0.30, p=0.020, y component: r=0.04, p=0.75, combined: r=0.26, p=0.04], mean velocity (dominated by horizontal velocity) [x component: r=0.33, p=0.010, y component: r=0.02, p=0.85, combined: r=0.33, p=0.010], and mean acceleration (dominated by x acceleration) [x component: r=0.32 p=0.011, y component: r=0.06, p=0.62, combined: r=0.31, p=0.016].

Figure 13:
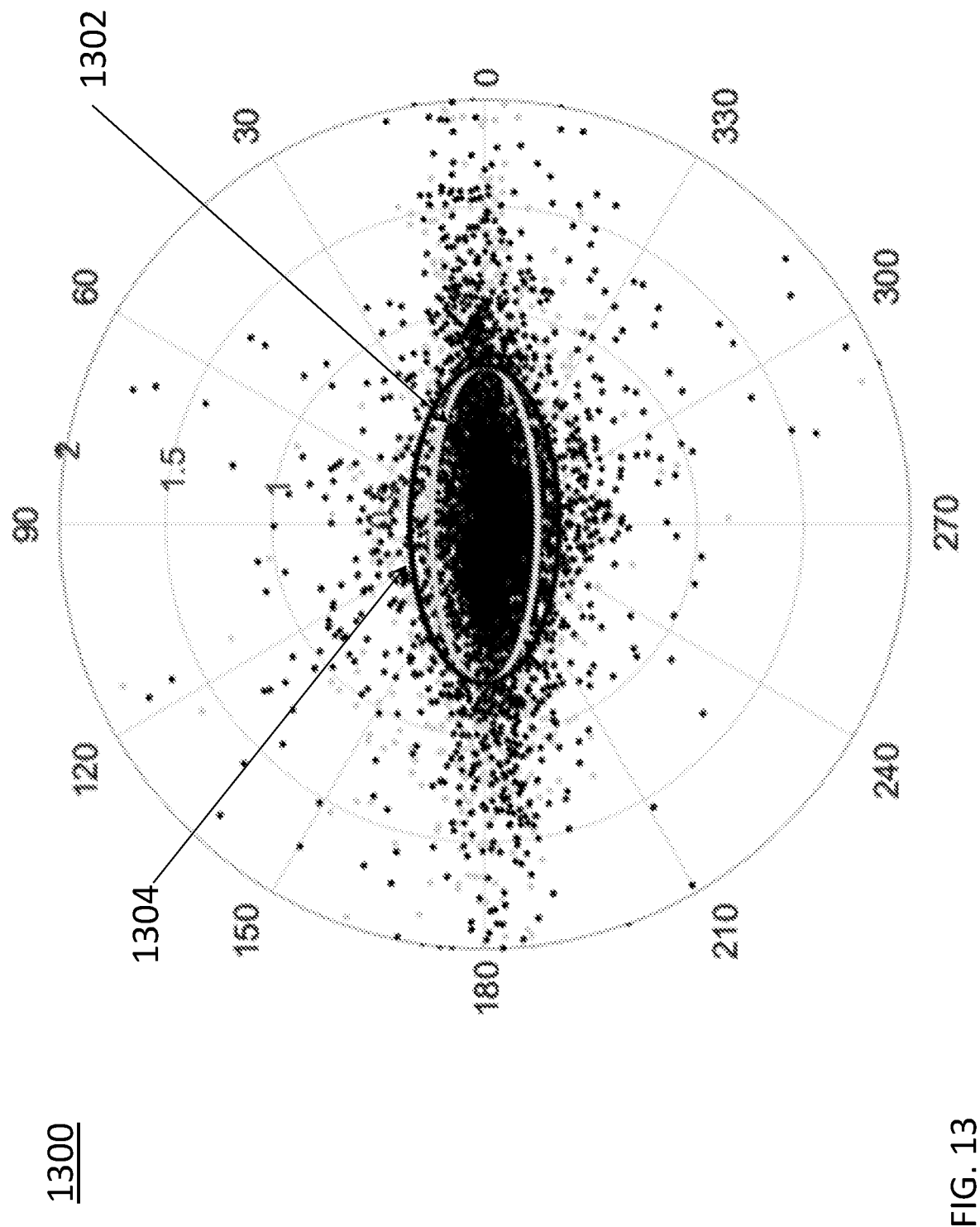
FIG. 13 depicts a polar plot of the amplitude and direction of 5,785 microsaccades made by MS patients and 4,779 made by controls during the 10-second TSLO recordings, consistent with some embodiments of the present invention.

FIG. 13 depicts a polar plot of the amplitude and direction of 5,785 microsaccades made by MS patients during the 10-second TSLO recordings in black. Ellipses 1302 corresponds to the 95% kernel density measurement of the MS participants. Ellipses 1304 corresponds to the 95% kernel density measurement of the healthy controls. The polar plot reveals that the amplitude of the microsaccades for MS participants is significantly different in the vertical amplitude of microsaccades than the horizontal. Thus, small changes in a vertical amplitude of microsaccades may be an indicator of and/or correlated with a greater neurological disruption and/or greater disability for MS patients than changes in horizontal amplitude.

In some embodiments, process 200 may be executed to correlate and/or draw comparisons between fixational eye motion to other diagnostic tests (e.g., same-day MRIs). Such correlations may facilitate better understanding of how fixational eye motion patterns change depending on brain lesion load, lesion location, and/or percent atrophy. Currently, roughly 76% of the 111 MS participants showed square wave jerk trains, nystagmus, a combination of the two, or ocular flutter. An over-arching goal is to use the TSLO eye-tracking system as a prognostic and monitoring tool for neurodegeneration.

Figure 3:
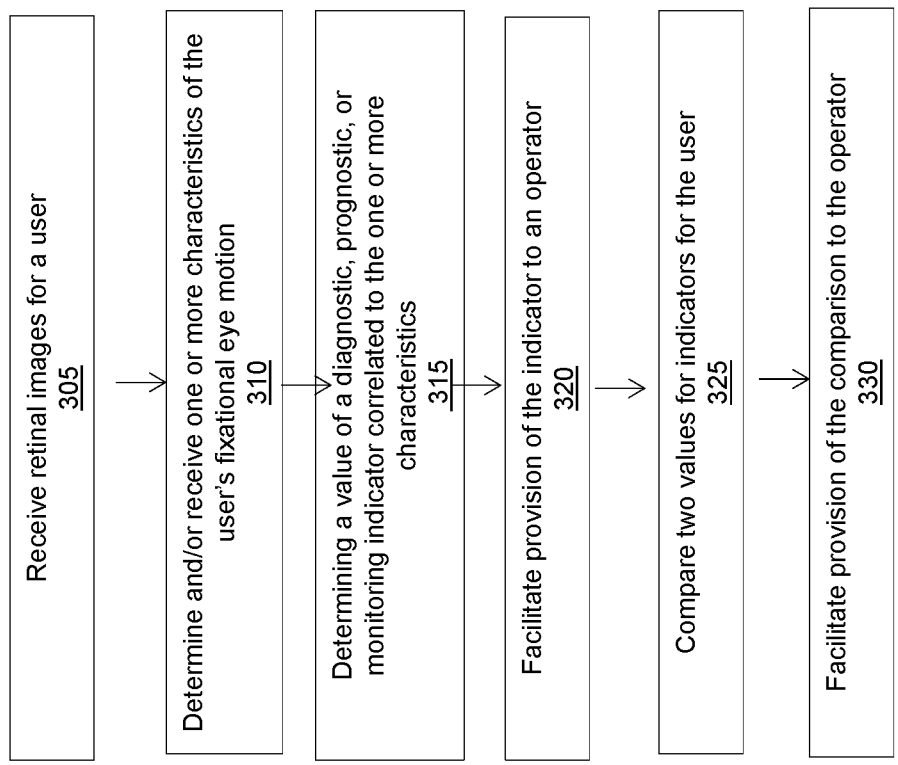
FIG. 3 depicts a flowchart showing a process for determining a value of a diagnostic indicator of a user's neurological health, consistent with some embodiments of the present invention.

FIG. 3 provides a flowchart illustrating a process 300 for determining a value of a diagnostic indicator of a user's neurological health. Process 300 may be performed by, for example, any system or system component disclosed herein.

Optionally, in step 305, retinal images, like retinal image 400 and/or the raw data used to generate a retinal image like retinal image 400 for one or both of a user's eye(s) may be received. When received, in step 310, the retinal images may be analyzed as described above to determine one or more characteristics thereof. Additionally, or alternatively, one or more characteristics of the user's fixational eye motion may be received in step 310. In some embodiments, a plurality of retinal images of an eye of the user prior to receipt of the one or more characteristics may be received in step 305 and a characteristic of the eye's fixational movement may be determined using the received retinal images as described herein.

In some embodiments, the characteristic of a user's fixational eye motion is a microsaccade measurement and/or a drift measurement. Additionally, or alternatively, the characteristic of a user's fixational eye motion may be one or more of a number of microsaccades in a time interval, an average number of microsaccades in a time interval, a peak number of microsaccades in a time interval, a raw or average amplitude of microsaccades in the time interval, a peak amplitude of microsaccades in the time interval, a velocity of microsaccades in the time interval, an average velocity of microsaccades in the time interval, a peak velocity of microsaccades in the time interval, a duration of microsaccades in the time interval, an average duration of microsaccades in the time interval, a peak duration of microsaccades in the time interval, an acceleration of microsaccades in the time interval, an average acceleration of microsaccades in the time interval, a peak acceleration of microsaccades in the time interval, a raw drift amplitude, an average drift amplitude, a peak drift amplitude, a drift duration, an acceleration in the vertical direction, a velocity in the vertical direction, a magnitude in the vertical direction, and/or a disconjugacy of any of the aforementioned motions between eyes.

In step 315, a value of a diagnostic indicator of a user's neurological health may be determined responsively to the one or more fixational eye motion characteristics. In some embodiments, execution of step 315 may include querying a data structure, like the data structure built/updated via process 200 (e.g., database 120) for a value of a diagnostic indicator that corresponds to the characteristic and/or the user's fixational eye motion. In some embodiments, the value for the diagnostic indicator may be estimated. Provision of the value of the diagnostic indicator to an operator (e.g., the user, a medical treatment provider, a researcher, etc.) may then be facilitated via, for example, display of the indicator on a display device (step 320).

In some instances, the user may be suffering from and/or may be seeking a diagnosis regarding a neurological condition such as, but not limited to, user's neurological health corresponds to a diagnosis of at least one of multiple sclerosis (MS), Parkinson's disease, Alzheimer's disease, dementia with Lewy bodies, frontotemporal dementia, Creutzfeldt-Jakob disease, vascular dementia, Wernicke-Korsakoff syndrome, amyotrophic lateral sclerosis (ALS), neuropsychiatric illnesses, Huntington's disease, brain damage, traumatic brain injury, mild traumatic brain injury, concussion, seizure disorders, cerebellar ataxia, epilepsy, peripheral neuropathy, movement disorders, demyelinating diseases, infections of the brain, stroke, brain tumors, and spinal cord tumors. At times, the user may be under the care of a physician for one or more of these medical conditions and process 300 may be executed to monitor the condition in order to determine, for example, responsiveness to therapy, disease progression, and/or remission.

At times, the value for the diagnostic indicator may correspond to a value of an expanded disability status scale (EDSS) score, a multiple sclerosis functional composite (MSFC) score, a raw symbol digit modality test (SDMT) score, an average SDMT score, a raw 9-hole peg test dominant score, an average 9-hole peg test dominant score, a raw 9-hole peg test nondominant score, an average 9-hole peg test nondominant score, a fatigue survey score, a global fatigue index (GFI) score, a functional systems score (FSS), a paced auditory serial addition test (PASAT) score, a lesion count, a lesion location, a lesion load, a percentage of atrophy of the user's brain, a percentage of atrophy of the user's spinal cord, a time to complete a 25 ft walk score, a serum-derived inflammatory marker score, a blood-derived inflammatory marker, a step count, optical coherence tomography (OCT) retinal layer thickness and angiography information, visually evoked potential (VEP) times/latencies, a cognitive score, a mood test score, an immediate post-concussion assessment and cognitive testing (ImPACT) score, a sport concussion assessment tool (SCAT) score, and a vestibular ocular motor screening (VOMS) score.

In some embodiments, a value for a plurality of diagnostic indicators of the user's neurological health may be determined responsively to the received characteristic via execution of step 315 and an indicator of the user's neurological health (e.g., degree of disability, disease state, rate of recovery, etc.) may be determined using the values for the plurality of diagnostic indicators.

In some embodiments, a plurality of characteristics of the user's fixational eye motion are received and/or determined in step 310 and the plurality may be analyzed to determine whether a pattern is present in the plurality of characteristics. Exemplary patterns include a square wave jerk pattern, a square wave jerk train pattern, nystagmus, an ocular flutter pattern, an ocular tremor pattern, and an internuclear ophthalmoplegia pattern and the determination of the value for the diagnostic indicator in step 315 may be based on the determined pattern.

In step 325, two or more values for diagnostic indicators may be determined and/or a value for a diagnostic indicator determined in step 315 may be compared with a previously determined diagnostic indicator and a result of this comparison may be provided to the operator (step 330). The two or more values for diagnostic indicators may be, for example, values for two more separate types of diagnostic indicators, values for the same diagnostic indicator for two different eyes, and/or values for the same diagnostic indicator taken at different times (e.g., minutes, days, weeks, months, and/or years apart). In some embodiments, the comparison may be used to determine an indicator of the user's neurological health, disease state, and/or rate of disease progression.

Figure 14:
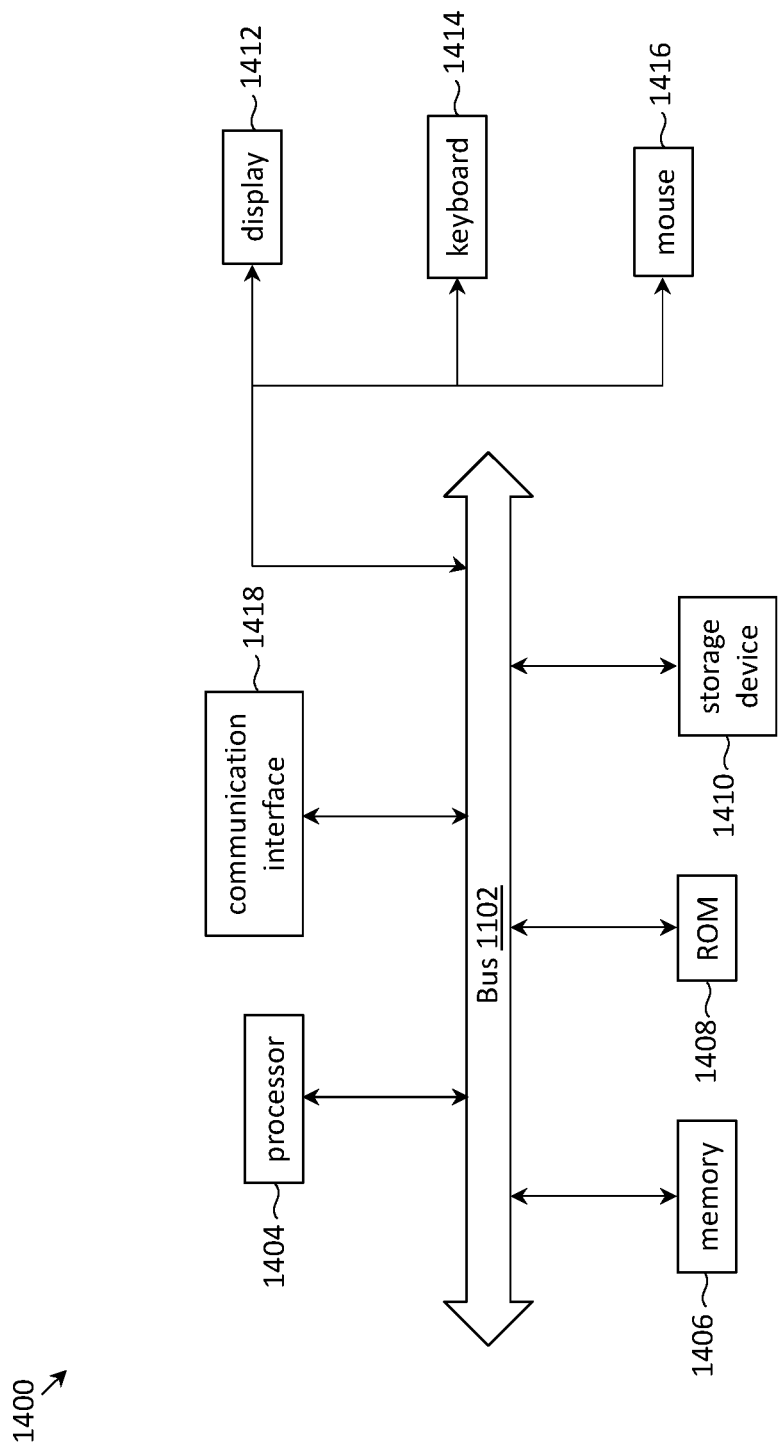
FIG. 14 depicts components of a computer system in which computer readable instructions instantiating the methods of the present invention may be stored and executed, consistent with some embodiments of the present invention.

As is apparent from the foregoing discussion, aspects of the present invention involve the use of various computer systems and computer readable storage media having computer-readable instructions stored thereon. FIG. 14 provides an example of a system 1400 that may be representative of any computing system that may be used to instantiate a neurological disease model and/or compute estimates of the value for a diagnostic indicator of a neurological disease. Examples of system 1400 may include a smartphone, a desktop, a laptop, a mainframe computer, an embedded system, etc. Note, not all of the various computer systems have all of the features of system 1400. For example, certain ones of the computer systems discussed above may not include a display inasmuch as the display function may be provided by a client computer communicatively coupled to the computer system or a display function may be unnecessary. Such details are not critical to the present invention.

System 1400 includes a bus 1402 or other communication mechanism for communicating information, and a processor 1404 coupled with the bus 1402 for processing information. Computer system 1400 also includes a main memory 1406, such as a random-access memory (RAM) or other dynamic storage device, coupled to the bus 1402 for storing information and instructions to be executed by processor 1404. Main memory 1406 also may be used for storing temporary variables or other intermediate information during execution of instructions to be executed by processor 1404. Computer system 1400 further includes a read only memory (ROM) 1408 or other static storage device coupled to the bus 1402 for storing static information and instructions for the processor 1404. A storage device 1410, for example a hard disk, flash memory-based storage medium, or other storage medium from which processor 1404 can read, is provided and coupled to the bus 1402 for storing information and instructions (e.g., operating systems, applications programs and the like).

Computer system 1400 may be coupled via the bus 1402 to a display 1412, such as a flat panel display, for displaying information to a computer user. An input device 1414, such as a keyboard including alphanumeric and other keys, may be coupled to the bus 1402 for communicating information and command selections to the processor 1404. Another type of user input device is cursor control device 1416, such as a mouse, a trackpad, or similar input device for communicating direction information and command selections to processor 1404 and for controlling cursor movement on the display 1412. Other user interface devices, such as microphones, speakers, etc. are not shown in detail but may be involved with the receipt of user input and/or presentation of output.

The processes referred to herein may be implemented by processor 1404 executing appropriate sequences of computer-readable instructions contained in main memory 1406. Such instructions may be read into main memory 1406 from another computer-readable medium, such as storage device 1410, and execution of the sequences of instructions contained in the main memory 1406 causes the processor 1404 to perform the associated actions. In alternative embodiments, hard-wired circuitry or firmware-controlled processing units may be used in place of or in combination with processor 1404 and its associated computer software instructions to implement the invention. The computer-readable instructions may be rendered in any computer language.

In general, all of the above process descriptions are meant to encompass any series of logical steps performed in a sequence to accomplish a given purpose, which is the hallmark of any computer-executable application. Unless specifically stated otherwise, it should be appreciated that throughout the description of the present invention, use of terms such as "processing", "computing", "calculating", "determining", "displaying", "receiving", "transmitting" or the like, refer to the action and processes of an appropriately programmed computer system, such as computer system 1400 or similar electronic computing device, that manipulates and transforms data represented as physical (electronic) quantities within its registers and memories into other data similarly represented as physical quantities within its memories or registers or other such information storage, transmission or display devices.

Computer system 1400 also includes a communication interface 1418 coupled to the bus 1402. Communication interface 1418 may provide a two-way data communication channel with a computer network, which provides connectivity to and among the various computer systems discussed above. For example, communication interface 1418 may be a local area network (LAN) card to provide a data communication connection to a compatible LAN, which itself is communicatively coupled to the Internet through one or more Internet service provider networks. The precise details of such communication paths are not critical to the present invention. What is important is that computer system 1400 can send and receive messages and data through the communication interface 1418 and in that way communicate with hosts accessible via the Internet. It is noted that the components of system 1400 may be located in a single device or located in a plurality of physically and/or geographically distributed devices.

Thus, an extremely accurate (e.g., 0.25 arcminute accuracy) and non-invasive retinal eye-tracking tool (i.e., the TSLO) to monitor patient disability and progression at the micron scale, in particular offering a non-invasive window into neurological health and motor function for MS patients, has been described.

What is claimed is:

1. A method, comprising:
   receiving, by a processor, a first plurality of retinal images for a left eye of the user;
   receiving, by the processor, a second plurality of retinal images for a right eye of the user;
   analyzing, by the processor, the first and second pluralities of retinal images to respectively determine a characteristic of microsaccades performed by the left eye of the user and a characteristic of microsaccades performed by the right eye of the user;
   comparing, by the processor, the characteristic of microsaccades performed by the user's left eye and the characteristic of microsaccades performed by the user's right eye;
   querying, by the processor, a database for a value for a diagnostic indicator of neurological disease that corresponds to a result of the comparison;
   receiving, by the processor, a value for a diagnostic indicator of neurological disease from the database responsively to the query; and
   providing, by the processor, the value for the diagnostic indicator of neurological disease to an operator.

2. The method of claim 1, wherein the determined characteristic includes one or more of:

a number of microsaccades in a time interval,
an average number of microsaccades in a time interval,
a peak number of microsaccades in a time interval,
a raw or average amplitude of microsaccades in the time interval,
a peak amplitude of microsaccades in the time interval,
a velocity of microsaccades in the time interval,
an average velocity of microsaccades in the time interval,
a peak velocity of microsaccades in the time interval,
a duration of microsaccades in the time interval,
an average duration of microsaccades in the time interval,
a peak duration of microsaccades in the time interval,
an acceleration of microsaccades in the time interval,
an average acceleration of microsaccades in the time interval, and
a peak acceleration of microsaccades in the time interval.

3. The method of claim 1, wherein the neurological disease includes one or more of multiple sclerosis (MS), Parkinson's disease, Alzheimer's disease, dementia with Lewy bodies, frontotemporal dementia, Creutzfeldt-Jakob disease, vascular dementia, Wernicke-Korsakoff syndrome, amyotrophic lateral sclerosis (ALS), neuropsychiatric illnesses, Huntington's disease, brain damage, traumatic brain injury, mild traumatic brain injury, concussion, seizure disorders, cerebellar ataxia, epilepsy, peripheral neuropathy, movement disorders, demyelinating diseases, infections of the brain, stroke, and brain tumors and spinal cord tumors.

4. The method of claim 1, wherein the analysis of the plurality of retinal images includes determining a plurality of microsaccade measurements, the method further comprising:
  determining whether a pattern is present in the plurality of microsaccade measurements.

5. The method of claim 4, wherein querying the database further includes querying the database for a neurological disease that corresponds to the determined characteristic of the microsaccades performed by at least one of the user's left eye and the user's right eye and the determined pattern.

* * * * *